United States Patent
Zupancic et al.

(10) Patent No.: US 7,094,912 B2
(45) Date of Patent: Aug. 22, 2006

(54) PROCESS FOR THE PREPARATION OF 4-OXYTETRAHYDROPYRAN-2-ONES

(75) Inventors: Silvo Zupancic, Novo mesto (SI); Dusan Krasovec, Sentrupert (SI); Pavel Zupet, Novo mesto (SI)

(73) Assignee: KRKA, Tovarna Zdravil, D. D., Novo Mesto (SI)

( * ) Notice: Subject to any disclaimer, the term of this patent is extended or adjusted under 35 U.S.C. 154(b) by 0 days.

(21) Appl. No.: 10/509,611

(22) PCT Filed: Mar. 17, 2003

(86) PCT No.: PCT/SI03/00009

§ 371 (c)(1),
(2), (4) Date: Sep. 27, 2004

(87) PCT Pub. No.: WO03/080591

PCT Pub. Date: Oct. 2, 2003

(65) Prior Publication Data

US 2005/0182263 A1    Aug. 18, 2005

(30) Foreign Application Priority Data

Mar. 26, 2002    (SI) ............... P-200200086

(51) Int. Cl.
*C07D 309/10* (2006.01)
(52) U.S. Cl. ................................ 549/292
(58) Field of Classification Search .......... 549/292
See application file for complete search history.

(56) References Cited

U.S. PATENT DOCUMENTS 5,393,893 A    2/1995 Kubela et al.

FOREIGN PATENT DOCUMENTS

| EP | 0 033 538 | 8/1981 |
|---|---|---|
| EP | 0 331 240 | 9/1989 |
| EP | 0 349 063 | 1/1990 |
| EP | 0 137 445 | 3/1990 |
| EP | 0 299 656 | 12/1990 |
| EP | 0 444 888 | 9/1991 |
| EP | 0 864 569 | 8/2001 |
| EP | 0 864 560 | 9/2004 |
| WO | WO 98/32751 | 7/1998 |
| WO | WO 00/46217 | 8/2000 |
| WO | WO 01/45484 | 6/2001 |
| WO | WO 01/72734 | 10/2001 |

OTHER PUBLICATIONS

J. Prakt., "Triethylamine Trishydrofluoride in Synthesis", Chem. 338 (1996) 99-113.

Dominique Pico et Daniel Anker, Utilisation du complexe triéthylamine acide fluorhydrique pour la synthèse de désoxyfluoropyranosides et al scission de groupes silylés substitutes.

*Primary Examiner*—Kamal A. Saeed
(74) *Attorney, Agent, or Firm*—Cohen, Pontani, Lieberman & Pavane

(57) ABSTRACT

A process for the preparation of inhibitors of HMG-CoA reductase, such as simvastatin, from 4-silyloxytetrahydropyran-2-ones with triethylamine trihydrofluoride being used as the desilylation reagent is described. The reaction is performed in organic solvents, a mixture thereof or without solvents. It is characteristic of this reaction that no additional impurities are obtained and that it takes place without the use of additional catalysts and with low excesses of the reagent.

17 Claims, No Drawings

US 7,094,912 B2

PROCESS FOR THE PREPARATION OF 4-OXYTETRAHYDROPYRAN-2-ONES

PRIORITY CLAIM

This is a U.S. national stage of application No. PCT/SI03/00009, filed on 17 Mar. 2003. Priority is claimed on that application and on the following application(s): Country: Slovenia, application No. P-200200086, Filed: 26 Mar. 2002.

FIELD OF THE INVENTION

The invention belongs to the field of organic chemistry and relates to a process for the preparation of inhibitors of HMG-CoA reductase such as simvastatin by desilylation of 4-silyloxytetrahydropyran-2-ones, preferably tert-butyldimethylsilyl-protected simvastatin, by the use of triethylamine trihydrofluoride reagent.

TECHNICAL PROBLEM

Due to their nature most known reagents for desilylation (removal of silyl protection group) cause the formation of by-products as well as the opening of the lactone ring, which is not desired. Thus, due to the formation of by-products, additional purifications and crystallizations of active substances have to be carried out. By the use of the said reagent these problems have been successfully solved.

BACKGROUND OF THE INVENTION

Prior Art

The knowledge of cholesterol metabolism and its role in the appearance of atherosclerosis as a coronary disease is of extraordinary importance in decreasing cardiovascular diseases. Nowadays hypercholesterolemia is treated by different pharmaceutically active substances such as lovastatin, pravastatin, simvastatin, mevastatin, atorvastatin, fluvastatin, cerivastatin and other derivatives and analogues known as inhibitors of HMG-CoA reductase (3 hydroxy-3-methylglutaryl coenzyme A).

The key step in the biosynthesis of cholesterol is a reduction of HMG-CoA into mevalonic acid resulting in the formation of more than one half of entire cholesterol in blood.

Several fermentation antihypercholesterolemics are obtained by means of different microorganism strains: *Aspergillus*, *Monascus*, *Amycolatopsis*, *Nocandia*, *Mucor*, and *Penicillinium*. Some of these new products are obtained by chemical methods from fermentation products, such as pravastatin and simvastatin, or they are synthetized by a multistep synthesis, e.g. fluvastatin and atorvastatin.

The processes for the preparation of simvastatin can be classified into two groups, namely the processes with a direct methylation of the side chain of lovastatin and the processes with a hydrolysis of lovastatin followed by the acylation of the hydroxy group on the hexahydro naphthalene ring.

The processes with the direct methylation of the side chain of lovastatin are described e.g. in EP 137445, EP 299656, WO 98/32751, U.S. Pat. No. 5,393,893, EP 864569, EP 864560.

The processes with acylation are described e.g. in EP 33538, wherein the synthesis of simvastatin is performed by deacylation of lovastatin followed by acylation of the obtained product with 2,2-dimethylbutanoyl chloride. This and similar processes for the synthesis of simvastatin and its derivatives and analogues use silyl protection of the 4-hydroxy group. There are known several processes for desilylation usually performed in a last synthesis step.

In EP 33538 the removal of the silyl protection group by the use of tetrabutylammonium fluoride (TBAF) in acetic acid is described, whereas EP 349063 describes the hydrolysis of silyl protection by TBAF in a mixture of acetic and triflouroacetic acid. The disadvantages of this reagent are its high price, the necessity to use tetrahydrofurane as the reaction solvent, which is difficult to regenerate, and the required 3–4 molar excess of the reagent with regard to the silyl-protected simvastatin.

In EP 331240 the use of HF in pyridine and acetonitrile is described. The use of HF is not suitable for industrial production due to the toxicity, great corrosiveness and difficult manipulation of the reagent.

EP 444888 describes the use of boron trifluoride etherate as a reagent for desilylation, which can take place in different solvents such as acetonitrile, THF, methylene chloride, ethyl acetate. The use of $BF_3$ etherate is not recommendable due to the inflammability of the reagent, particularly on a larger, industrial scale.

In performing the removal of protection groups of 4-silyloxytetrahydropyran-2-ones with methanesulfonic acid such as decribed in WO 01/2734, an opening of the lactone ring occurs, therefore in this process an additional synthesis step of closing the lactone ring is required.

In WO 00/46217 the use of ammonium fluoride and ammonium hydrogen difluoride in the presence of an acid such as acetic acid is described. A disadvantage of this process is that a poorly crystallizable product is obtained, which affects the purity and the yield of the product having to be purified by column chromatography or alternate crystallization from water-miscible and water-immiscible solvents.

In WO 01/45484 the use of concentrated HCl is described. A disadvantage of this process is the formation of considerable amounts of simvastatin acid, about 10%, which requires an additional step of lactonization, wherein the formation of a dimeric impurity occurs. It is stated in the description and in the Examples that the lactonization is performed in methylene chloride in the presence of an acid e.g. p-toluenesulfonic acid, which means that the step of protection removal is followed by the step of lactonization, wherein the formation of dimeric impurity occurs.

The reagent TEA.3HF (triethylamine trihydrofluoride) is known from the literature as both a fluorination and desilylation reagent as described in J. Pract. Chem./Chem.-Ztg. (1996), 338 (2), 99–113. In JP 8027152 its use for desilylation of carbapenem silyl esters is stated and in U.S. Pat. No. 5,552,539 its use for desilylation in a process for the synthesis of ribonucleic acids is described. In Carbohydrate Research 166 (1987), 309–313, there is cited the use of this reagent for desilylation of primary alcohols with the reaction giving good yields.

SUMMARY OF THE INVENTION

Description of the Invention

The object of the present invention is a process for the preparation of 4-oxytetrahydropyran-2-ones of the formula I

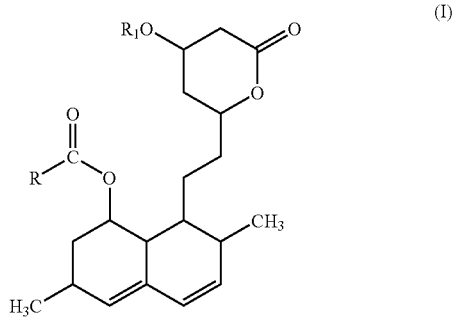

wherein
R means a $C_{1-12}$-alkyl group and
$R_1$ means H, in which in a compound of the formula (I), wherein R has the above meaning and $R_1$ means a silyl protection group, the silyl protection group is removed by the use of triethylamine trihydrofluoride in an organic solvent, a mixture of organic solvents or without a solvent, and the obtained compound is isolated.

The compounds of the formula (I), wherein $R_1$ means H, are effective antihypercholesterolemic compounds and their most charasteristic representative is simvastatin.

The group R in the formula (I) can mean a branched or a straight $C_{1-12}$-alkyl group or a cyclic $C_{3-10}$-alkyl group, preferably a $C_5$-alkyl group, especially $CH_3CH_2C(CH_3)_2$-group.

Protection groups $R_1$ are silyl protection groups used for the protection of hydroxy groups, such as trisubstituted silyl groups e.g. trimethylsilyl, triethylsilyl, dimethylisopropylsilyl, tert-butyldimethylsilyl, (triphenylmethyl)dimethylsilyl, tert-butyldiphenylsilyl, diisopropylmethylsilyl, triisopropylsilyl, triphenylsilyl, diphenylmethylsilyl, diethylisopropylsilyl, dimethylhexylsilyl, tribenzylsilyl, tri-p-xylylsilyl, tert-butylmethoxyphenylsilyl, preferably tert-butyldimethylsilyl and trimethylsilyl groups.

The process for the preparation of compounds of formula (I), wherein $R_1$ means H, is performed in such a way that a compound of formula (I), wherein $R_1$ means a silyl protection group, is treated by TEA.3HF in an organic solvent, a mixture of organic solvents or without a solvent. As the organic solvent there can be used halogenated organic solvents, hydrocarbons, aromatic hydrocarbons, esters, ethers, amides, amines, nitrites, carbonates, sulfoxides, e.g. 1,4-dioxane, butyl acetate, isopropyl acetate, ethyl acetate, methylene chloride, acetonitrile, dimethylsulfoxide, dimethylformamide, dimethylacetamide, toluene, xylene, tetrahydrofurane, dimethylcarbonate, diethylcarbonate, cyclohexane, triethylamine and other organic solvents and mixtures of organic solvents. The desilylation reaction can be performed in a temperature range from 0° C. to the boiling point of the organic solvent or the reaction mixture, preferably in a range between room temperature and 50° C.

Since the desilylation reagent TEA.3HF contains 3 moles of HF in the molecule, it is, in practice, used in an amount from 0.3 moles on to 1 mole of the protected compound of formula (I), preferably from 0.3 to 1.5 moles to 1 mole of the protected compound of formula (I). The duration of the reaction depends on the selected conditions such as the temperature, the solvent, the excess of the reagent.

After the completed desilylation reaction, which is quantitative at optimum conditions, less than 1% of the starting compound remains in the reaction mixture and not essential opening of the lactone ring takes place. It is characteristic of this reaction step that no additional impurities such as simvastatin dimer, simvastatin acetate ester, exomethylene simvastatin, dehydrosimvastatin, which can be very problematic in processes known from the prior art, are obtained.

In the further course of purification only impurities formed in previous phases are quantitatively removed. For the isolation of a compound of formula (I), wherein $R_1$ means H, known and standard processes can be used.

Thus, after the completed desilylation the reaction mixture can be diluted with a weakly polar solvent such as hydrocarbons; aromatic hydrocarbons e.g. toluene; ethers e.g. tert-butyl ether, diethyl ether; esters e.g. ethyl acetate, propyl acetate, isopropyl acetate, butyl acetate, isobutyl acetate, tert-butyl acetate; halogenated hydrocarbons e.g. methylene chloride and the like.

After completed washings the organic phase is concentrated and the product is precipitated with nonpolar solvents such as alkanes e.g. hexane, heptane, cyclohexane; petroleum ether; halogenated hydrocarbons e.g. methylene chloride, chloroform and chlorobutane. After isolation the obtained crude product is very pure, HPLC area purity above 98.5%.

If necessary, the product can be recrystallized by known processes from a solvent or a solvent mixture such as alcohols e.g. methanol, ethanol, isopropanol, tert-butanol; ketones e.g. butyl methylketone, acetone; water; acetonitrile aromatic hydrocarbons e.g. toluene; alkanes e.g. cyclohexane hexane, heptane, petroleum ether; halogenated hydrocarbons e.g. chlorobutane, methylene chloride, dichloroethane, chloroform; esters e.g. methyl acetate, ethyl acetate, propyl acetate, butyl acetate and other solvents.

The starting substance of formula (I), tert-butyldimethylsilyloxy simvastatin, can be prepared according to the known processes from the prior art cited e.g. in EP 33538, EP 287340 and WO 99/43665.

Tert-butyldimethylsilyloxy simvastatin prepared according to the known prior art processes is in the form of an oily product that is very difficult to purify.

We have suprisingly found that the starting substance can also be isolated in a solid form. Thus, when the well evaporated oily compound tert-butyldimethylsilyloxy simvastatin is cooled in such a manner that a partial or complete solidification of the oil occurs and the product is subsequently dissolved in heptane and cooled again, a product is precipitated in the solution. This product is filtered off and dried in a vacuum dryer. The so obtained product has a $T_{m.p.}$ from 50 to 58° C. and HPLC area purity 98.82%.

Therefore, an object of the present invention is also tert-butyldimethylsilyloxy simvastatin in solid form.

A further object of the present invention is the use of tert-butyldimethylsilyloxy simvastatin in solid form for the preparation of simvastatin.

The advantage of the process according to the present invention is that by desilylation of the protected simvastatin with TEA.3HF, a considerably smaller degree of hydrolysis of the lactone ring occurs, which has been a problem in hitherto known processes.

An advantage of the reagent TEA.3HF is that it is liquid and soluble in organic solvents so that the desilylation can be performed without the addition of a solvent or in solvents, which are at the same time also used as extraction solvents, such as acetates e.g. ethyl acetate, propyl acetate, isopropyl acetate, butyl acetate; aromatic hydrocarbons e.g. toluene, xylene; halogenated hydrocarbons e.g. dichloromethane, trichloromethane; ethers e.g. tert-butyl methyl ether or cyclohexane, and other organic solvents or mixtures of organic solvents. This makes the isolation essentially easier in technological and ecological sense.

A further advantage of the reagent TEA.3HF is that it has a low molecular weight and contains three moles of bound fluoride in a molecule, whereas e.g. TBAF contains only one mole of bound fluoride and its molecular weight is almost twice the size. For these reasons an essentially smaller quantitative amount of the reagent is consumed, which makes its use economically and technologically more favourable. The reagent TEA.3HF is industrially available, inexpensive and effective.

An advantage of the use of TEA.3HF for the desilylation of the compounds of the formula (I), wherein $R_1$ means a silyl protection group, is that the reaction is performed in a series of organic solvents without the use of additional catalysts such as acids e.g. acetic, trifluoracetic and other acids.

Further advantages of the use of this reagent for desilylation are also that it is gentle and less corrosive. This reagent has a pH of 4 and therefore the desilylation reaction can be performed in stainless and glass reactors. At desilylation there do not occur any coloration of the products, formation of byproducts and opening of the lactone ring occur.

According to the present invention a product with essentially higher yields without additional purification steps is obtained. Regarding the use of solvents, the desilylation and the isolation can be performed in the same solvent, which essentially simplifies the process for the preparation of simvastatin.

DETAILED DESCRIPTION OF THE PRESENTLY PREFERRED EMBODIMENTS

The present invention is illustrated but not limited by the following Examples.

1. Reference Example According to the Process of WO 00/46217

Silylated simvastatin (5.097 g, 9 mmole) was dissolved in acetic acid (20 ml) and the mixture was heated to 45° C., whereupon $NH_4F$ (3.636 g, 9.8 mmole) was added and the reaction mixture was stirred in an inert atmosphere at a temperature of 45–50° C. for 5 hours. Then the reaction mixture was left to cool, slightly evaporated and extracted twice with 18 ml of heptane and three times with 18 ml of a mixture of toluene:EA in a ratio 10:1. Then the toluene phases were washed with 22.7 ml of water and three times with 9 ml of a saturated $NaHCO_3$ solution. The organic phase was evaporated to the dryness.

The residue was crystallized from a methanol/water mixture and an oily product (HPLC area 94.98%) was obtained.

The disadvantage of the process is that the product is obtained in the form of an oil, which makes the purification process more difficult and even after crystallization a product of inadequate quality is obtained.

2. Reference Example According to the Process of WO 01/45484

Silylated simvastatin (10 mmole) was dissolved in THF (48 ml) and 1,4-dioxane (2.5 ml) was added thereto and the mixture was cooled to 0° C. Then conc. HCl (3.5 ml) was added and the reaction mixture was stirred at this temperature in an inert atmosphere for 6 hours.

HPLC area % of reaction mixture after that time:

| Simvastatin | Simvastatin acid | Simvastatin dimer |
|---|---|---|
| 75.73% | 8.89% | 0.34% |

The pH value of mixture was adjusted to 1.5 by the addition of triethylamine and then it was evaporated to the residue at a temperature below 30° C. Thereto 40 ml of ethyl acetate and 40 ml of water were added and the mixture was stirred, separated and the organic phase was washed with 40 ml of a saturated NaCl solution. The organic phase was dried over $MgSO_4$, filtered and evaporated at a temperature below 35° C. An oily residue (5.75 g) was obtained, which was dissolved in 35 ml of dichloromethane. To this solution p-toluenesulfonic acid (0.07 g) was added and it was stirred at room temperature for 1 hour.

HPLC area % of reaction mixture after that time:

| Simvastatin | Simvastatin acid | Simvastatin dimer |
|---|---|---|
| 83.62% | 0.48% | 5.71% |

Then the mixture was evaporated at a temperature below 30° C. and an oily residue (5.62 g) was obtained. This residue was dissolved in 15 ml of ethyl acetate at 40–60° C. and 60 ml of hexane were added thereto. Then the mixture was stirred for one hour at room temperature and two hours at 0° C. The precipitate was filtered off and dried. 2.18 g (52%) of the precipitate were obtained. The precipitate was dissolved in 50 ml of methanol, active charcoal was added and it was stirred for 30 minutes. After filtration of active charcoal, additional 50 ml of water were added and it was left to cool at 0° C. for two hours. The product was filtered off and dried in a vacuum dryer for two hours. 1.61 g (38.5%) of the product were obtained.

The disadvantage of the process is a considerable opening of the lactone ring up to 10%, which requires an additional lactonization step, wherein additional impurities such as dimer impurity may appear. The quality and the yield of the product are inadequate.

EXAMPLE 1

Silylated simvastatin (5.5 mmole) was dissolved in tetrahydrofurane (10 ml) and TEA.3HF (0.41 ml, 2.2 mmole) was added thereto and the reaction mixture was stirred in an inert atmosphere at room temperature for 46 hours. The course of reaction was completed with less than 0.05% of simvastatin acid—area % HPLC. Then the reaction mixture was diluted with 50 ml of ethyl acetate and washed with 50 ml of water, 30 ml of 5% brine and three times with 30 ml of a saturated $NaHCO_3$ solution. After treating the organic phase with active charcoal, it was dried by azeotropic evaporation of the solvent. The final product was precipitated by the addition of 7 ml of heptane. After cooling the suspension the product was filtered off. 1.75 g (76.1%) of simvastatin of an adequate purity were obtained.

EXAMPLE 2

Silylated simvastatin (5.5 mmole) was dissolved in DMSO (10 ml) and TEA.3HF (0.58 ml, 3.0 mmole) was added thereto and the reaction mixture was stirred in an inert atmosphere at 40° C. for 23 hours. The course of reaction was completed with less than 0.06% of simvastatin acid—area % HPLC. Then the reaction mixture was left to cool to room temperature and was diluted with 12.5 ml of ethyl acetate and 25 ml of water. Then the mixture was stirred and separated and the organic phase was washed with 25 ml of 5% brine, twice with 19 ml of saturated NaHCO$_3$ solution and once with 19 ml of saturated brine. After treating the organic phase with active charcoal, it was dried by azeotropic evaporation of a solvent. The final product was precipitated by the addition of 7 ml of heptane. After cooling the suspension the product was filtered off. 1.65 g (71.8%) of simvastatin of an adequate purity were obtained.

EXAMPLE 3

Silylated simvastatin (11 mmole) was dissolved in ethyl acetate (20 ml) and TEA.3HF (1.8 ml, 9.4 mmole) was added thereto and the reaction mixture was stirred in an inert atmosphere at 35° C. for 19 hours. The course of reaction was completed. Then the reaction mixture was left to cool to room temperature, diluted with 25 ml of ethyl acetate and washed with 50 ml of water, 50 ml of 5% brine, twice with 50 ml of a saturated NaHCO$_3$ solution and once with 37 ml of saturated brine. After treating the organic phase with active charcoal, it was dried by azeotropic evaporation of the solvent. The final product was precipitated by the addition of 13 ml of heptane. After cooling the suspension the product was filtered off. 3.50 g (76.1%) of simvastatin of an adequate purity were obtained.

EXAMPLE 4

Preparation of tert-butyldimethylsilyloxy Simvastatin in a Solid Form

Well evaporated oily compound tert-butyldimethylsilyloxy simvastatin was left to cool at a temperature up to 5° C. overnight, whereat a partly or complete solidification of the oil occured. This product was dissolved in heptane and left to cool and the precipitated solid product was filtered off. The solid product was dissolved once more in heptane and filtered and it was left to cool overnight. The precipitated product was filtered off and dried in a vacuum dryer. A product with a melting point of 50–58° C. and HPLC area 98.82% was obtained.

What is claimed is:

1. A process for the preparation of 4-oxytetrahydropyran-2-ones of the formula I

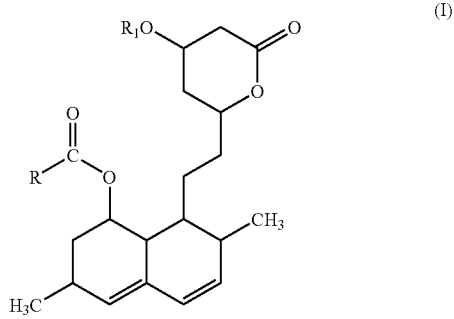

Wherein
R means a $C_{1-12}$-alkyl group and
R$_1$ means H,
comprising the steps of a) providing a compound of the formula (I), wherein R has the above meaning and R$_1$ means a silyl protection group, b) removing the silyl protection group by triethylamine trihydrofluoride in an organic solvent, a mixture of organic solvents or without an organic solvent, and c) isolating the obtained compound.

2. The process according to claim 1, wherein the group R in the formula (I) is a branched or straight $C_{1-12}$-alkyl group or a cyclic $C_{3-10}$-alkyl group.

3. The process according to claim 1, wherein the silyl protection group R$_1$ in the formula (I) is a trisubstituted silyl protection group.

4. The process according to claim 3, wherein the trisubstituted silyl protection group is selected from the group consisting of trimethylsilyl, triethylsilyl, dimethylisopropylsilyl, tert-butyldimethylsilyl, (triphenylmethyl)dimethylsilyl, tert-butyldiphenylsilyl, diisopropylmethylsilyl, triisopropylsilyl, triphenylsilyl, diphenylmethylsilyl, diethylisopropylsilyl, dimethylhexylsilyl, tribenzylsilyl, tri-p-xylylsilyl, tert-butylmethoxyphenylsilyl, preferably tert-butyldimethylsilyl, and trimethylsilyl groups.

5. The process according to claim 1, wherein it is performed without a catalyst.

6. The process according to claim 1, wherein the organic solvent or the mixture of organic solvents are selected from the group consisting of halogenated organic solvents, hydrocarbons, aromatic hydrocarbons, esters, ethers, amides amines, nitriles, carbonates, sulfoxides, e.g. 1,4-dioxane, butyl acetate, isopropyl acetate, ethyl acetate, methylene chloride, acetonitrile, dimethylsulfoxide, dimethylformamide, dimethylacetamide, toluene, xylene, tetrahydrofurane, dimethylcarbonate, diethylcarbonate, cycloxehane, and triethylamine.

7. The process according to claim 1, wherein the isolation of the obtained compound is performed in the same organic solvent.

8. The process according to claim 7, wherein the organic solvent that is used is an acetate, aromatic hydrocarbon halogenated hydrocarbon, ether and mixtures thereof.

9. The process according to claim 8, wherein the acetate is ethyl acetate, propyl acetate, or isopropyl acetate.

10. The process according to claim 8, wherein the aromatic hydrocarbon is toluene or xylene.

11. The process according to claim 8, wherein the halogenated hydrocarbon is dichloromethane or trichloromethane.

12. The process according to claim 8, wherein the ether is tert-butyl methyl ether.

13. The process according to claim 1 which is performed at a temperature from 0° C. to the boiling point of the organic solvent or the reaction mixture.

14. The process according to claim 13, which is performed at a temperature from room temperature to 50° C.

15. The process according to claim 1, wherein from 0.3 mole to 1.5 mole of triethylamine trihydrofluoride is reacted with 1 mole of the silylated product.

16. The process according to claim 2 wherein R in the formula (I) is $C_5$-alkyl group.

17. The process according to claim 16 wherein R is CH$_3$CH$_2$C(CH$_3$)$_2$.

* * * * *